(12) United States Patent  (10) Patent No.: US 6,438,200 B1
Kita  (45) Date of Patent: Aug. 20, 2002

(54) X-RAY FLUORESCENCE ANALYZING APPARATUS

(75) Inventor: Hiroaki Kita, Osaka (JP)

(73) Assignee: Rigaku Industrial Corporation, Takatsuki (JP)

( * ) Notice: Subject to any disclaimer, the term of this patent is extended or adjusted under 35 U.S.C. 154(b) by 0 days.

(21) Appl. No.: 09/663,697

(22) Filed: Sep. 22, 2000

(51) Int. Cl.⁷ ............................................. G01N 23/223
(52) U.S. Cl. .......................................... 378/44; 378/45
(58) Field of Search .............................. 378/44, 45, 46; 709/200; 714/11, 37, 39

(56) References Cited

U.S. PATENT DOCUMENTS

| | | | |
|---|---|---|---|
| 4,764,945 A | * 8/1988 | Tadahiro | 378/50 |
| 5,366,896 A | 11/1994 | Margrey et al. | |
| 5,757,659 A | 5/1998 | Arai et al. | |
| 6,035,328 A | * 3/2000 | Soukal | 709/217 |
| 6,173,036 B1 | * 1/2001 | Hossain et al. | 378/45 |
| 6,259,675 B1 | * 7/2001 | Honda | 370/248 |
| 6,272,235 B1 | * 8/2001 | Bacus et al. | 382/133 |
| 6,272,437 B1 | * 8/2001 | Woods et al. | 702/35 |

FOREIGN PATENT DOCUMENTS

| | | | |
|---|---|---|---|
| DE | 91 01 148 | 6/1991 | |
| DE | 93 05 189 | 9/1994 | |
| EP | 0 293 624 A2 | 12/1988 | |
| JP | 2000250873 | * 9/2000 | ........... G06F/15/16 |
| WO | WO 98/26295 | 6/1998 | |

OTHER PUBLICATIONS

GIT Labor–Fachzeitschrift, 1/99, pp. 60–61.
Chemie Ingenieur Technik, 10/96, pp. 1311–1313.
Spectrometry Solutions, Bruker Analytical X–Ray Systems.

* cited by examiner

Primary Examiner—Robert H. Kim
Assistant Examiner—Irakli Kiknadze
(74) Attorney, Agent, or Firm—Antonelli, Terry, Stout & Kraus, LLP

(57) ABSTRACT

An analyzing apparatus, comprising: a single main body (1); a single main computer (2), being connected to the main body directly, and enabling analysis operations by the main body; and sub-computers (4, 5) being connected to the main computer (2) through a network (3), wherein real-time display about progress of analysis and/or reference to results of analysis are available, as well as off-line operation thereof, on either one of the sub-computers (4, 5) through which the operation is not made for the analysis.

9 Claims, 1 Drawing Sheet

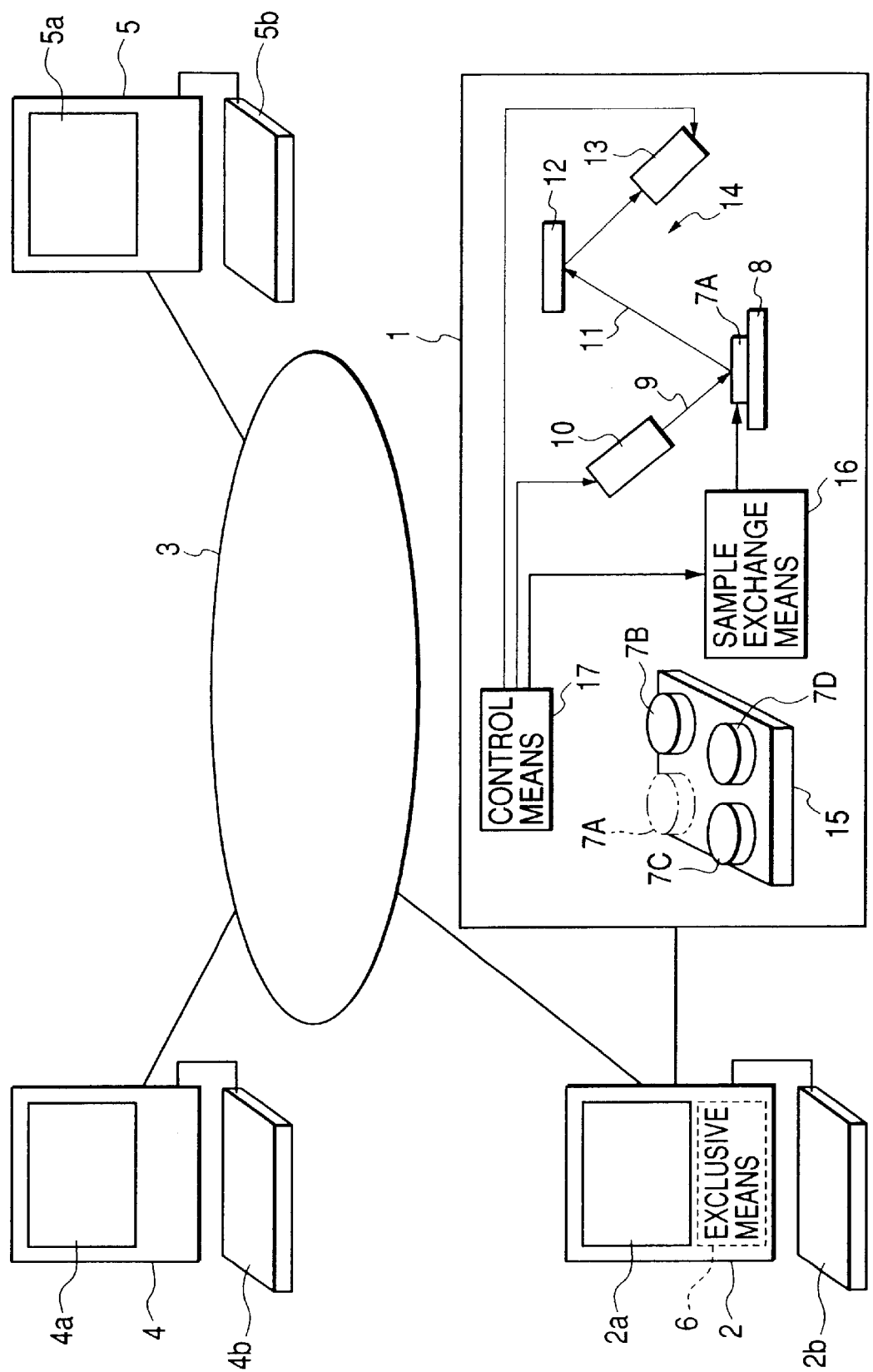

X-RAY FLUORESCENCE ANALYZING APPARATUS

BACKGROUND OF THE INVENTION

1. Field of the Invention

The present invention relates to an analyzing apparatus for analyzing samples, and in particular relates to the analyzing apparatus which comprises a plural number of computer apparatuses therein.

2. Description of Prior Art

Conventionally, in particular in the X-ray fluorescence analyzer, etc., there was already known an analyzing apparatus, which comprises a single main body of the apparatus, a main computer being directly connected thereto for enabling analyzing operation thereof, and a sub-computer, being connected to the main computer through a network and enabling display of a progress or advance in analysis, etc., whereby the progress of analysis can be seen or checked even from the sub-computer which is located at a distance and does not perform the analyzing operation, but not through the main computer which is located in a neighbor of the main body of the apparatus.

However, in a system wherein on the sub-computer can be displayed the progress of analysis, etc., on real-time, only a keyboard and a mouse are further provided in addition thereto, so as to display a screen same to that of the main computer, but it is impossible to perform operations being different from those made by the main computer. Also, in a system wherein the progress or result of analysis is read out by the sub-computer while once being written into a file within the main computer, it is impossible to perform the real-time display of the progress or result of analysis therewith.

SUMMARY OF THE INVENTION

An object, according to the present invention, for dissolving the problems of the conventional arts mentioned above, is to provide an analyzing apparatus for analyzing samples, comprising a plurality of computers therein, wherein by means of the computer which does not perform the analyzing operation, it is possible to perform, not only the real-time display of the progress and the result of analysis, but also off-line operations, including comparison or reference to the result of analysis.

First, according to the present invention, for accomplishing the above-mentioned object, there is provided an analyzing apparatus, comprising: a single main body; a single main computer, being connected to said main body directly, and enabling analysis operations by said main body; and a sub-computer being connected to the main-computer through a network, wherein, at least, real-time display about progress and results of analysis being executed in that-main body, and off-line operations; including reference to the results of the analysis being executed in the main body, are available on said sub-computer.

With such the structure of the apparatus mentioned in the above, in more detail, information is transmitted on real-time, from the main computer to the sub-computer through the network, by means of socket communication (i.e., a network address combining an IP address corresponding to an address within a network, which is owned by a computer conducting the communication by means of TCP/IP, and a port number which is a sub- (or auxiliary) address of the IP address), therefore the progress and results of the analysis can be displayed on the sub-computer which does not execute the analysis operation therewith, and also the off-line operations, such as the reference to the results of the analysis, is available therewith.

Further, according to the present invention, there is also provided an analyzing apparatus, comprising: a single main body, operation of which is controlled by a control means; a single main computer, being connected to said main body directly, and enabling analysis operations by said main body; and a sub-computer, being connected to said main body through a network and said main computer, and enabling the analysis operations by said main body, wherein, either one of said main computer or said sub-computer has an exclusive means for excluding an analysis operation that brings the control means of said main body to be disable, and at least, real-time display about progress and results of, analysis being executed in said main body, and off-line operations, including reference to the results of the analysis executed in said main body, are available on either one of said main computer or said sub-computer, on which no analysis operation is executed.

According to such the structure of the apparatus mentioned in the above, in more detail, with provision of such the exclusive means, the analysis operation can be executed smoothly by using the plural number of computers, i.e., the main computer and the sub-computer. Also, being similar to the apparatus mentioned above, the real-time display about the progress and results of the analysis can be made on either the main computer or the sub-computer, on which no analysis operation is made.

Further, according to the present invention, there is also provided a X-ray fluorescence analyzer apparatus, measuring strength of X-ray fluorescence generated by irradiation of primary X-ray upon the sample, having the same structure as the analyzing apparatus mentioned above. And, with this analyzer apparatus, it is also possible to obtain the same effect mentioned in the above.

Furthermore, according to the present invention, there is also provided a X-ray fluorescence analyzer apparatus, measuring intensity of X-ray fluorescence generated by irradiation of primary X-ray upon the sample, having the same structure as the analyzing apparatus mentioned above. And, with this analyzer apparatus, it is also possible to obtain the same effect mentioned in the above. dr

DESCRIPTION OF THE DRAWINGS

FIG. 1 is an outline view for showing a X-ray fluorescence analyzer, according to an embodiment of the present invention.

DESCRIPTION OF PREFERRED EMBODIMENTS

Hereinafter, the X-ray fluorescence analyzer as an embodiment according. to the present invention will be fully explained by referring to. the attached drawings.

First. of all,.-explanation will be given on the structure of this apparatus, by referring to the FIG. 1. This apparatus, i.e., the so-called the X-ray fluorescence analyzer, in a single main body 1 of the apparatus, comprises: a sample table 8 on which samples 7 are disposed, a X-ray source 10 for irradiating a primarily X-ray 9 onto the sample 7, such-as a X-ray tube, etc., and a detection means 14, including an analyzing crystal 12 and a detector 13, etc. Also, for analyzing the plural samples 7A, 7B . . . continuously, it comprises a waiting table 15 for keeping them waiting, and a sample exchanging means 16 for moving the sample 7 between the waiting table 15 and the sample table 8, so as to exchange the sample 7 to be analyzed, such as a robot hand, etc. Control operations of the sample exchanging means 16, the X-ray source 10 and the detection means 14, etc., are conducted by means of a microcomputer (control means) 17 which is installed within the main body.

This apparatus also comprises a single main computer 2 for enabling the analyzing operations in the main body 1, which is disposed in neighbor of the main body 1 and is connected directly thereto, but not through such as a network. Further, the apparatus comprises, for example, two (2) sets of sub-computers 4 and 5 for also enabling the analyzing operations in the main body 1, which are connected to the main body 1 through a network 3, such as a LAN, etc., and to the main computer 2. In more detail, information is transmitted from the main computer 2 to the sub-computers 4 and 5 through the network 3, by means of so-called the socket communication, on real-time. Each of the computers 2, 4 and 5 has a display means 2a, 4a or 5a, such as a CRT, and an input means 2b, 4b or 5b, such as a keyboard, etc., respectively. The main body 1 of the apparatus and the main computer-2 are located in a laboratory, for example, while the first sub-computer 4 and the second sub-computer 5 are in a conference room-and a office, for example,; respectively. Through the network 3, such as a telephone circuit or the Internet, etc., the main body 1 and the main computer 2 may be located in the laboratory in Osaka (i.e., the name of city in Japan) while the sub-computers 4 and 5 in a factory or works in Tokyo (the city located at long distance from Osaka).

The main computer 2 has an exclusive means 6 provided for excluding the analysis operations, such as those bringing the microcomputer 17 in the main body 1 to be unable to perform the processing thereof. Herein, the analysis. operations mean, for example, setting of the sample to be analyzed, positioning of the sample 7A to be analyzed on the sample table 8, irradiation of the primary X-ray 9 thereupon, start of measurement, exchange of the samples 7, completion of the measurement, stoppage of irradiation of the primary X-ray 9, etc. The exclusive means 6 may be provided in the first sub-computer 4 or in the second sub-computer 5.

Further, with such the apparatus, by means of the main computer 2 or the sub-computer 4 or 5, which does not perform the analyzing operations, the real-time display of progress of analysis is by the main body 1 and the off-line operations, such as setting up of analysis condition and the comparison or reference of the result of analysis, are available. Herein, the progress of analysis means a condition of progress in the series of analyzing operations mentioned above, or an abnormality that the analyzing operations do not advance smoothly or satisfactorily, etc., while the analysis results means results of analyzing calculations which are made on percentage contents about each of the samples 7A, 7B . . . , upon the basis of measured values thereof.

Next, explanation will be given on the operation of this apparatus. First of all, for example, a certain operator puts or mounts a plural number of samples 7A, 7B . . . to be analyzed on.-the waiting table 15 of the main body 1, and she/he sets up the analysis: conditions, so as to execute the analysis operations. Namely, setting the samples 7 to be analyzed, the sample 7A to be analyzed first is mounted on the sample table 8, and the primary X-ray 9 is irradiated thereupon, thereby starting the measurement thereof. After that, in normal, the -operations are performed, such. as an analysis calculation or computation upon basis of the measured values, the exchange of the sample 7, the completion of measurement, and the stoppage of irradiation of the primary X-ray 9, etc., one by one automatically.

Herein, according to this apparatus, the operator, who-goes out of the laboratory to her/his office, for example, is able to see or check the progress of analysis (including an error in the analysis) and/or the result of analysis, on real-time, upon the display means 5a of the second sub-computer 5 which is located in the office, and is further able to execute the off-line operations, such as seeing the analysis results made up to then, from the second sub-computer 5, etc. And, depending upon the progress on the analysis, she/he is also able to do the analysis operations, such as the completion of analysis, etc., or also other analysis operations, such as re-start of measurement after setting up the analysis conditions again, via off-line operations, from the second sub-computer 5. Other various analysis operations are also available to be executed from those computers 2, 4 and 5, not be restricted only to the above.

Furthermore, the sub-computers 4 and 5 are connected to the main body 1 through the main computer 2 which has the exclusive means 6 mentioned above, therefore it is possible to obtain smooth analysis operations among the plural number of the computers 2, 4 and 5. For example, in a case where, after execution of the analysis operation, such as starting of the measurement, from the main computer 2, another operator who does not know that also tries to execute the analysis operation, i.e., the starting of the measurement from the first sub-computer 4, a warning message, such as "The measurement was already started from the computer in the laboratory.", etc., is displayed on the display means 4a of the first sub-computer 4, thereby preventing the instructions for starting the measurement provided from the both computers from being sent to the microcomputer 17 of the main body 1 at random. Accordingly, the another operator can notice a reasonable reason why she/he cannot perform the analysis operation, while there is no possibility that the microcomputer 17 in the main body 1 comes to be unable to perform the processing.

Also, for example, in a case where, during when the analysis operation for setting up the samples to be analyzed is executed from the second sub-computer 5 which is located in the office, while another operator who does not know that also tries to execute the analysis operation for resetting the samples to be analyzed, from the main computer 2 which is located in the laboratory, a warning message, such as "Now, setting of sample to be analyzed is made from the computer in the office.", etc., is displayed on the display means 2a of the main computer 2, and thereby preventing the instructions for starting the measurement provided from the both computers from being sent to the microcomputer 17 of the main body 1 at random. Accordingly, also the another operator can notice a reasonable reason why she/he cannot perform the analysis operation, while there is no possibility that the microcomputer 17 in the main body 1 comes to be unable in the processing.

Herein, for example, when no analysis operation is executed via the main computer 2, it is possible to display the progress and the results of analysis made within the main body 1 upon the display means 2a of the main computer 2, on real-time, even if the analysis operations are executed by the other one, i.e., the first sub-computer 4 or the second sub-computer 5, therefore the off-line operations are available, including the comparison or reference to the results: of analysis made by the main body 1. In the above, the communication among those computers 2, 4 and 5 are made through the network 3, by using the, socket communication.

However, a portion or all of the main computer 2 may be built in within the main body 1, or may be unified with the microcomputer 17 provided within the main body 1. And, according to the present embodiment, the analysis calculation itself is conducted only by the main computer 2, upon the basis of the measured values. Also, it is possible to install a large scale program software for the analysis calculation into the other computers 4 and 5, however in this case there occurs a waste that the same analysis calculation is executed by the plural number of the computers at the same time.

As was mentioned in detail in the above, according to the present invention, with the analyzing apparatus for analyzing the samples, comprising a plurality number of computers therein, wherein, by using the computer which does not execute the analysis operations therein, it is possible to perform the off-line operations, such as the real-time display of the progress and the results of the analysis, as well as the reference of the analysis results thereof.

What is claimed is:

1. An analyzing apparatus, comprising:
    a single main body, operation of which is controlled by a control means;
    a single main computer, being connected to said main body directly, and enabling analysis operations by said main body; and
    a sub-computer, being connected to said main body through a network and said main computer, and enabling the analysis operations by said main body, wherein,
        either one of said main computer or said sub-computer has an exclusive means for excluding an analysis operation that brings the control means of said main body to be disable, and
        at least, real-time display about progress and results of analysis being executed in said main body, and off-line operations, including reference to the results of the analysis executed in said main body, are available on either one of said main computer or said sub-computer on which no analysis operation is executed.

2. An analyzing apparatus according to claim 1, wherein the analyzing apparatus is an X-ray fluorescence analyzer, and the single main body includes means for irradiating a primary X-ray upon a sample, and means for measuring strength of X-ray fluorescence generated by irradiation of the primary X-ray upon the sample, the single main computer enabling analysis operations relating to the X-ray fluorescence.

3. An analyzing apparatus according to claim 2, wherein said sub-computer enables analysis operations by said main body.

4. An analyzing apparatus according to claim 1, wherein said sub-computer enables at least one analyzing operation by said main body which is the same as an analyzing operation by said main body enabled by said single main computer.

5. An analyzing apparatus according to claim 1, wherein both of said main computer and said sub-computer have the exclusive means for excluding an analysis operation that brings the control means of said main body to be disabled.

6. A X-ray fluorescence analyzer apparatus, measuring strength of X-ray fluorescence generated by irradiation of primary X-ray upon a sample, comprising:
    a single main body, operation of which is controlled by a control means;
    a single main computer, being connected to said main body directly, and enabling analysis operations by said main body; and
    a sub-computer, being connected to said main body through a network and said main computer, and enabling the analysis operations by said main body, wherein,
        either one of said main computer or said sub-computer has an exclusive means for excluding an analysis operation that brings the control means of said main body to be disable, and
        at least, real-time display about progress and results of analysis being executed in said main body, and off-line operations, including reference to the results of the analysis executed in said main body, are available on either one of said main computer or said sub-computer on which no analysis operation is executed.

7. An X-ray fluorescence analyzer apparatus according to claim 6, wherein the single main body includes means for irradiating a primary X-ray upon a sample, and means for measuring strength of X-ray fluorescence generated by irradiation of the primary X-ray upon the sample, the single main computer enabling analysis operations relating to the X-ray fluorescence.

8. An X-ray fluorescence analyzer apparatus according to claim 7, wherein said sub-computer enables analysis operations by said main body.

9. An X-ray fluorescence analyzer apparatus according to claim 6, wherein said sub-computer enables at least one analyzing operation by said main body which is the same as an analyzing operation by said main body enabled by said single main computer.

* * * * *